US00PP13526P2

(12) United States Plant Patent
Zaiger et al.

(10) Patent No.: US PP13,526 P2
(45) Date of Patent: Jan. 28, 2003

(54) INTERSPECIFIC TREE NAMED 'YUBA GOLD'

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 10/055,858

(22) Filed: Jan. 25, 2002

(51) Int. Cl.[7] ..... A01H 5/00
(52) U.S. Cl. ..... Plt./180
(58) Field of Search ..... Plt./180

*Primary Examiner*—Bruce R. Campell
*Assistant Examiner*—Anne Marie Grünberg

(57) ABSTRACT

A new and distinct variety of interspecific tree, originating from various varieties of *Prunus persica* var. *nucipersica* and *Prunus persica* crossed with *Prunus salicina*. The following features of the tree and its fruit are characterized with the tree budded on 'Nemaguard' Rootstock (non-patented), grown on Handford sandy loam soil with Storie Index rating 95 in USDA Hardiness Zone 9, near Modesto, Calif., with standard commercial fruit growing practices such as pruning, thinning, spraying, irrigation and fertilization. Its novelty consists of the following unique combination of features that are desirable in a new variety.

1. Heavy and regular production of relatively uniform size fruit.
2. Clingstone fruit with non-melting, firm, yellow flesh.
3. Fruit that maintains excellent shape, texture, color and good flavor after being canned.
4. Vigorous, upright growth of tree.

1 Drawing Sheet

BACKGROUND OF THE VARIETY

STATEMENT REGARDING FEDERALLY SPONSORED RESEARCH OR DEVELOPMENT

Not applicable.

Field of the Invention

In the field of plant genetics, we conduct an extensive and continuing plant-breeding program including the organization and asexual reproduction of orchard trees, of which almonds, apples, apricots, cherries, peaches, plums, nectarines and interspecifics are exemplary. It is against this background of our activities that the present variety of interspecific tree was originated and asexually reproduced by us in our experimental orchard located near Modesto, Stanislaus County, Calif.

PRIOR VARIETIES

Among the existing varieties of interspecific, nectarine and plum trees, which are known to us and mentioned herein, are 'Autumn Grand' Nectarine (U.S. Plant Pat No. 2,894), 'Royal Giant' Nectarine (U.S. Plant Pat. No. 4,107) and Interspecific tree 'Citation' (U.S. Plant Pat. No. 5,112).

ORIGIN OF THE VARIETY

The new and distinct variety of interspecific tree [*Prunus persica* var. *nucipersica*×((*Prunus persica*×(*Prunus salicina*×*Prunus persica*))] was developed by us in our experimental orchard as an open pollinated seedling from seed collected from the proprietary parent with field identification number 27RC248. The maternal parents of 27RC248 originated from a cross between the nectarines 'Autumn Grand' Nectarine (U.S. Plant Pat. No. 2,894) and 'Royal Giant' Nectarine (U.S. Plant Pat. No. 4,107). The paternal parent of 27RC248 originated from a non-melting peach seedling of unknown parentage crossed with the Interspecific tree 'Citation' (U.S. Plant Pat. No. 5,112). A large number of these open pollinated seedlings were planted and grown on their own root system, during which time we recognized the potential of the desirable fruit characteristics for processing as a non-melting, clingstone interspecific and, in 1992, selected it for asexual propagation and commercialization.

ASEXUAL REPRODUCTION OF THE VARIETY

Asexual reproduction of the new and distinct variety of interspecific tree was by budding, in 1992, to 'Nemaguard' Rootstock (non-patented) as performed by us in our experimental orchard located near Modesto, Calif., and shows that all reproductions run true to the original tree and all characteristics of the tree and its fruit are established and transmitted through succeeding asexual propagations.

SUMMARY OF THE VARIETY

The present new interspecific tree [*Prunus persica* var. *nucipersica*×(*Prunus persica*×(*Prunus salicina*×*Prunus persica*))] is of large size, vigorous upright growth and a productive and regular bearer of medium size, non-melting, yellow flesh, clingstone fruit, maintaining an excellent shape, texture, appearance and flavor after being canned. The fruit is further characterized by having very firm flesh, ripening relatively uniform throughout the tree and having good shipping and storage quality. After the fruit is cut and exposed to the air, it has a very low tendency toward browning or discoloration of flesh. In comparison to the paternal non-melting peach parent, it has greater production of more uniform fruit. In comparison to the 'Autumn Grand' and 'Royal Giant' nectarines, it has non-melting flesh, compared to melting flesh and the skin has pubescence compared to glabrous skin.

PHOTOGRAPH OF THE VARIETY

The accompanying color photographic illustrations show typical specimens of the foliage and fruit of the present new interspecific variety. The illustration shows the upper and lower surface of the leaves, an exterior and sectional view of the fruit divided in the suture plane to show flesh color, pit cavity and a stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit as based on observations of a 7 year old specimen grown near Modesto, Calif., with color terminology in accordance with Munsell Book of Color.

Tree:

*Size.*—Large. Pruned to 3 to 3.5 meters in height at maturity for economical harvesting of fruit.

*Vigor.*—Vigorous. Growth of 1.5 to 2 meters the first growing season. Varies with soil fertility and cultural practices.

*Form.*—Upright. Usually pruned to vase shape.

*Branching habit.*—Upright. Crotch angle approximately 35° . Heavy fruit production increases crotch angle.

*Productivity.*—Productive. Usually sets 1½ to several times the amount of fruit desired, thinning and spacing necessary.

*Density.*—Medium dense. Pruning to vase shape by removing branches and foliage from center of tree to increase sunlight and air movement throughout the tree.

*Bearer.*—Regular bearer. Has had heavy production 6 consecutive years. No alternate bearing observed.

*Fertility.*—Self fertile. Abundant pollen.

*Hardiness.*—Hardy in all stone fruit growing areas of california. Trees grow in USDA Hardiness Zone 9. Winter chilling requirement of approximately 800 hours at or below 45° F.

Trunk:

*Size.*—Large, stocky. Average circumference 46.9 cm at 30.4 cm above ground on a 7 year old tree.

*Texture.*—Medium shaggy, becomes rougher with age.

*Color.*—10R 5/2 to 10R 6/2. Color darkens with age.

Branches:

*Size.*—Medium to large. Average circumference 17.14 cm at 1 meter above the ground. Crotch angle approximately 35°. Angle increases with heavy crop load.

*Texture.*—Smooth to medium rough. Varies with age of growth.

*Lenticels.*—Average number of 25 in 25.8 square cm surface. Average length 3.5 mm. Average width 1.0 mm. Color 7.5YR 4/8 to 7.5YR 5/8, becomes darker with age.

*Color.*—New growth 2.5GY 5/6 to 2.5GY 6/6. Old growth 5YR 4/4 to 5YR 5/6. Varies with age of growth.

Leaves:

*Size.*—Average length 142.6 mm. Average width 35.1 mm.

*Form.*—Lanceolate.

*Apex.*—Acuminate.

*Base.*—Cuneate.

*Margin.*—Serrate.

*Thickness.*—Medium.

*Surface.*—Upper surface relatively smooth, slight indentation over midrib and leaf veins, glabrous. Lower surface relatively smooth, small ridges created by midrib and pinnate venation, glabrous. Midrib color l0Y 7/4.

*Petiole.*—Average length 9.6 mm. Average width 1.3 mm. Longitudinally grooved. Glabrous. Color 10Y 6/8.

*Glands.*—Reniform. Medium to large. Average length 1 mm. Average diameter 0.6 mm. Number — varies from 2 to 4, average number 3. Location — upper portion of petiole and base of leaf blade. Color 2.5GY 5/4.

*Color.*—Upper surface 5GY 4/4. Lower surface 5GY 5/4.

Flower buds:

*Size.*—Medium size. Average length 14.4 mm. Average diameter 6.47 mm.

*Form.*—Plump, conical, becoming elongated before opening.

*Hardiness.*—Hardy in all stone fruit growing areas of California.

*Pubescence.*—Pubescent on outer surface of sepal.

*Color.*—2.5R 6/8 to 2.5R 7/8.

*Pedicel.*—Average length 2.6 mm. Average width 2.2 mm. Color 2.5GY 8/10.

Flowers:

*Size.*—Medium, non-showy. Average height 18.3 mm. Average diameter 24.1 mm.

*Petals.*—Five, alternately arranged to sepals. Orbicular. Average length 11.6 mm. Average width 11.7 mm. Margin varies from entire to sinuate. Color 2.5R 7/8, fades with age.

*Sepals.*—Number — 5, alternately arranged to petals. Shape — triangular, apex roughed. Pubescence — inner surface glabrous. Outer surface pubescent. Average length 4.4 mm. Average width 3.3 mm. Color — upper surface 5GY 7/6. Outer surface 2.5YR 3/6.

*Stamens.*—Average number per flower 40. Average length 11.9 mm. Average filament color 2.5GY 9/2. Anther color 5R 3/10.

*Aroma.*—Slight.

*Pollen.*—Present, self fertile.

*Pistil.*—Normally 1, varies from 1 to 2. Average length 17.6 mm. Surface is pubescent. Color 2.5GY 9/6. Average 1.6 mm lower than stamens.

*Blooming period.*—Date of First Bloom Feb. 26, 2001. Date of Petal Fall Mar. 9, 2001. Varies slightly with climatic conditions.

*Color.*—2.5R 7/8.

*Pedicel.*—Short in length. Average length 2.8 mm. Average width 2.4 mm. Color 2.5GY 8/8.

*Number of flowers per flower bud.*—Normally one.

Fruit:

*Maturity when described.*—Firm ripe.

*Date of first picking.*—Jul. 28, 2001.

*Date of last picking.*—Aug. 3, 2001. Varies slightly with climatic conditions.

*Size.*—Medium. Average diameter axially 62.3 mm. Average transversely in suture plane 71.3 mm. Average weight 162.73 grams.

*Form.*—Nearly globose. Slightly retuse at base.
*Suture.*—Shallow. Extends from base to apex.
*Ventral surface.*—Nearly rounded. Only slightly lipped.
*Apex.*—Rounded.
*Base.*—Retuse.
*Cavity.*—Rounded to slightly elongated in suture plane. Average depth 7.8 mm. Average breadth 9.8 mm.

Skin:
*Thickness.*—Medium, tenacious to flesh.
*Surface.*—Medium smooth, without roughness or reticulation.
*Pubescence.*—Pubescent, moderate amount. Relatively short. No tendency to roll when rubbed.
*Tendency to crack.*—None.
*Color.*—7.5YR 7/12.
*Astringency.*—Undetected.

Stem:
*Size.*—Medium. Average length 6.1 mm. Average width 3.1 mm.
*Color.*—Varies from 2.5GY P/4 to 2.5GY 8/6.

Flesh:
*Ripens.*—Evenly.
*Texture.*—Firm, meaty, non-melting.
*Firmness.*—Firm, non-melting.
*Fibers.*—Few, small, tender.
*Aroma.*—Slight.
*Amydgalin.*—Undetected.
*Eating quality.*—Good.
*Canning quality.*—Very good. Maintaining an excellent shape, texture, appearance and flavor after being canned four consecutive years.
*Juice.*—Moderate for non-melting flesh.
*Color.*—10YR 8/8. Pit cavity 10YR 7/10.

Stone:
*Type.*—Clingstone.
*Size.*—Medium. Average length 26.9 mm. Average width 21.4 mm. Average thickness 18.9 mm.
*Form.*—Obovate.
*Base.*—Varies from rounded to straight.
*Apex.*—Acute, very short.
*Sides.*—Equal to unequal. Most stones uniform, some with one side extending further from suture plane.
*Surface.*—Pitted toward base. Pits vary from round to elongated. Irregularly furrowed toward apex, furrows vary in length.
*Ridges.*—Relatively wide, nearly smooth.
*Tendency to split.*—Very slight.
*Color.*—7.5YR 4/8, when dry.

Kernal:
*Form.*—Oblong, pointed on embryo end.
*Taste.*—Bitter.
*Viability.*—Viable, complete.
*Size.*—Medium. Average length 18.4 mm. Average width 11.6 mm. Average thickness 5.3 mm.
*Skin color.*—Varies from 5YR 5/8 to 5YR 5/10, when dry.

Use: Canning. Market — local and long distance.

Keeping quality: Good, held firm for 2 weeks in cold storage at 380 to 42√ F. without appreciable shriveling or loss of firmness.

Shipping quality: Good, showed minimal bruising of flesh or skin scarring during picking, packing and shipping trials.

Plant disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific tree, substantially as illustrated and described, characterized by its regular and heavy production of medium size, yellow flesh, non-melting, clingstone fruit with the ability to maintain excellent shape, texture, flavor and appearance after being canned. The fruit is further characterized by ripening evenly, having good shipping and handling qualities and a low browning characteristic to the flesh after being sliced.

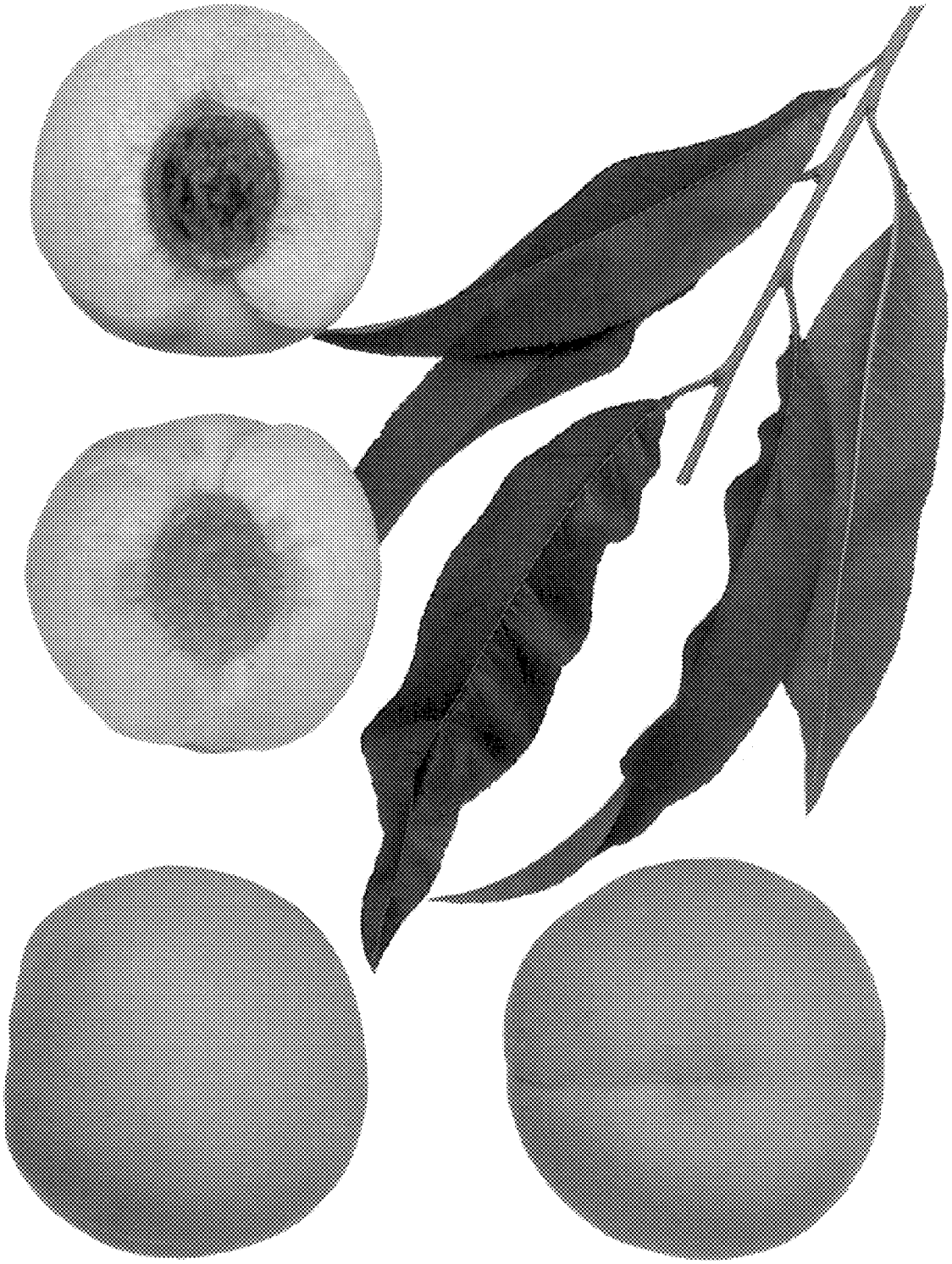

* * * * *